United States Patent
Meyer et al.

(10) Patent No.: US 7,481,220 B2
(45) Date of Patent: Jan. 27, 2009

(54) BREATHING MASK WITH BREATHING GAS SUPPLY THROUGH THE STRAP

(75) Inventors: Jörg-Uwe Meyer, Ratzeburg (DE); Götz Kullik, Lübeck (DE); Cornelia Schrader, Lübeck (DE); Hans-Ullrich Hansmann, Barnitz (DE)

(73) Assignee: Drägerwerk Aktiengesellschaft, Lübeck (DE)

( * ) Notice: Subject to any disclaimer, the term of this patent is extended or adjusted under 35 U.S.C. 154(b) by 230 days.

(21) Appl. No.: 11/082,528

(22) Filed: Mar. 17, 2005

(65) Prior Publication Data

US 2005/0284481 A1   Dec. 29, 2005

(30) Foreign Application Priority Data

Jun. 23, 2004  (DE)  .................. 10 2004 030 068

(51) Int. Cl.
*A62B 18/08* (2006.01)
*A62B 18/00* (2006.01)
*A62B 18/02* (2006.01)
*A61M 15/00* (2006.01)
*A61M 16/00* (2006.01)

(52) U.S. Cl. .................. 128/207.11; 128/200.27; 128/204.18; 128/205.25; 128/206.27; 128/204.11

(58) Field of Classification Search ............ 128/201.22, 128/201.23, 201.29, 205.25, 206.13, 206.27, 128/207.11, 207.17, 207.18, DIG. 26, 846, 128/869, 202.18, 206.19

See application file for complete search history.

(56) References Cited

U.S. PATENT DOCUMENTS

| | | | | | |
|---|---|---|---|---|---|
| 2,259,817 | A | * | 10/1941 | Hawkins | 128/207.18 |
| 2,270,313 | A | * | 1/1942 | Kraft | 601/44 |
| 3,333,585 | A | * | 8/1967 | Barghini et al. | 128/201.13 |
| 3,554,135 | A | * | 1/1971 | Duvall et al. | 410/119 |
| 3,599,636 | A | * | 8/1971 | Gutman et al. | 128/207.11 |
| 4,018,221 | A | * | 4/1977 | Rennie | 128/207.18 |
| 4,194,247 | A | * | 3/1980 | Melander | 2/457 |
| 4,297,999 | A | * | 11/1981 | Kitrell | 128/205.16 |
| 4,437,462 | A | * | 3/1984 | Piljay et al. | 128/207.11 |
| 4,848,366 | A | * | 7/1989 | Aita et al. | 128/863 |
| 4,951,662 | A | * | 8/1990 | Townsend, Jr. | 128/205.25 |
| 5,481,763 | A | * | 1/1996 | Brostrom et al. | 2/452 |
| 5,485,832 | A | * | 1/1996 | Joffity | 128/201.11 |
| 6,588,424 | B2 | * | 7/2003 | Bardel | 128/207.11 |
| 6,718,981 | B2 | * | 4/2004 | Cardarelli | 128/206.19 |
| 6,889,689 | B1 | * | 5/2005 | Neuman | 128/201.22 |
| 6,928,657 | B2 | * | 8/2005 | Bell et al. | 2/9 |
| 6,938,620 | B2 | * | 9/2005 | Payne, Jr. | 128/848 |

(Continued)

OTHER PUBLICATIONS

Croakies; Eyeglass retaining structure; Sep. 14, 2006; http://www.croakies.com/eyewearretainers/eyewearsport/images color /SER rl 2c f4.gif.

*Primary Examiner*—Justine R Yu
*Assistant Examiner*—Annette F Dixon
(74) *Attorney, Agent, or Firm*—McGlew & Tuttle, P.C.

(57) ABSTRACT

A breathing mask to be fastened with a strap on the head with breathing gas supply through the strap. The strap includes areas that have a multilayer design and at least two layers of the material of the strap lying one on top of another are connected with one another such that they form a channel, through which a gas can flow.

25 Claims, 2 Drawing Sheets

U.S. PATENT DOCUMENTS

| | | | |
|---|---|---|---|
| 6,941,949 B2* | 9/2005 | Amante et al. | 128/206.21 |
| 2004/0078860 A1* | 4/2004 | Bell et al. | 2/9 |
| 2005/0056278 A1* | 3/2005 | Ogilvie | 128/201.22 |
| 2005/0061326 A1* | 3/2005 | Payne, Jr. | |
| 2005/0121030 A1* | 6/2005 | Bateman et al. | 128/201.23 |
| 2005/0284481 A1* | 12/2005 | Meyer et al. | 128/207.11 |

* cited by examiner

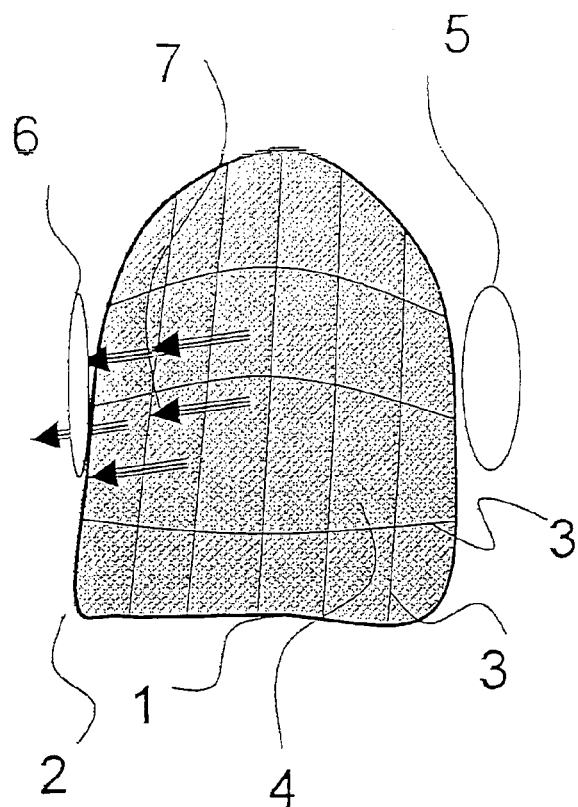
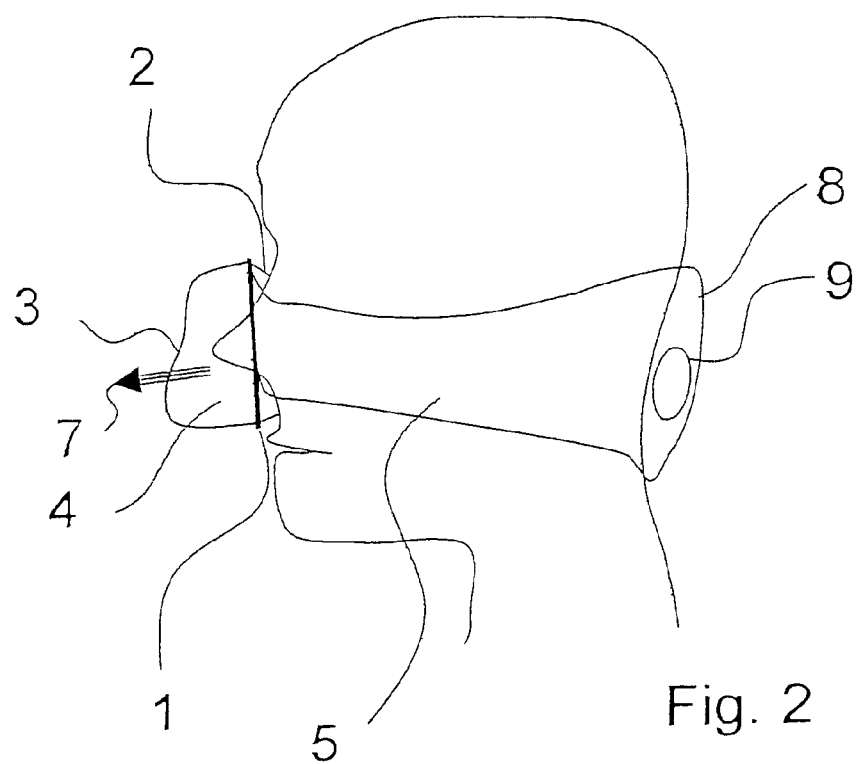
Fig. 1
Fig. 2

BREATHING MASK WITH BREATHING GAS SUPPLY THROUGH THE STRAP

CROSS REFERENCE TO RELATED APPLICATIONS

This application claims the benefit of priority under 35 U.S.C. § 119 of DE 10 2004 030 068.2 filed Jun. 23, 2004, the entire contents of which are incorporated herein by reference.

FIELD OF THE INVENTION

The present invention pertains to a breathing mask with breathing gas supply through the strap.

BACKGROUND OF THE INVENTION

One application of such breathing masks is represented by so-called CPAP (continuous positive airway pressure) respirators. Patients who require respiratory support for various reasons, for example, sleep apnea or COPD (chronic obstructive pulmonary disease), are frequently treated with such CPAP respirators. A settable overpressure is now made available to the patient for supporting the respiration. The supply is usually with constant pressure over the entire breathing cycle, the set pressure being made available via a breathing mask. These breathing masks are usually designed as nose or mouth-and-nose masks, which are connected, for supplying the breathing mask, with flexible tubes, via which they are supplied from a CPAP respirator. The expired breathing air usually escapes through an expiration valve, which is frequently integrated within the mask. In addition, a humidifier or a combined heat/moisture exchanger is frequently present.

Since the diseases treated with such breathing masks are often illnesses that are underestimated by the patients affected, it is important for a successful therapy that the devices to be used, including the breathing masks, find sufficient acceptance by the users in order to be used regularly. However, the wearing of breathing masks is usually linked with negative associations and is felt to be highly uncomfortable. The wearing of a breathing mask seems to be an expression of being in need of help because of an already manifest disease. The putting on of the mask by means of a strap and the use of separate flexible tubes for feeding the breathing gas from the respirator or CPAP respirator to the breathing mask creates a highly technical mechanical impression. Moreover, the feed via the flexible tube frequently takes place via the patient's forehead, which can be felt as an accentuation of the manifestation of being dependent on a machine and, moreover, it greatly compromises recognizability in a facial area that determines the facial expressions. The disfigurement seemingly associated with the therapy even leads to rejection of such a therapy in extreme cases. Another problem in the acceptance of prior-art breathing masks is the nuisance associated with the generation of noise during expiration, which is due to the model of the breathing mask. The expiration valve usually comprises a simple hole, which is arranged directly in the mask or in the immediate vicinity of the mask, or a plurality of openings, which may be complicated. A gas flow corresponding to the overpressure being provided is continuously escaping from these openings into the environment. The use of individual holes as an expiration valve in or on CPAP masks leads to a locally occurring, high velocity of flow in the immediate vicinity of these holes. This high velocity of flow turns the expiration valve into a disturbing source of noise.

Besides the generation of noise, the focusing of escaping gas flows represents an additional drawback. A gas flow hitting the surfaces of the face, especially in the area of the patient's eyes, may be usually felt to be highly unpleasant and may lead to complaints, especially in the area of the eyes.

The amount of gas that can be discharged from the discharge valves is determined essentially by the flow resistance of the discharge valves. On the one hand, the amount of gas should be as small as possible in order to keep possible nuisances in terms of the generation of noise and the draft resulting from focused gas flows as low as possible. On the other hand, a minimum permeability is necessary, because no appreciable increase in pressure is to take place in the area of the mask during the expiration by the patient, which takes place against the constant pressure being provided anyway. If a great increase in pressure is to be avoided during expiration, it is, moreover, desirable not to allow the velocities of flow to rise above a point at which changeover of the laminar flow into a turbulent flow takes place. There is only a linear increase in the volume flow with the existing pressure difference in the laminar flow range. This dependence no longer applies if there is a changeover into a turbulent flow with increasing velocity of flow. There will now be a very rapid pressure rise even during a slight further increase in the volume flow through the expiration valves, because the flow resistance increases greatly. This increasing pneumatic resistance is felt by the patient to be very unpleasant. It is therefore known that the expiration valve should be designed as an array of many small discharge openings. As a result, the volume flow being discharged is divided into many individual flows, and only low velocities of flow are reached even in case of large volume flows that pass through the expiration valve. However, such valves are additional complex components and they frequently cannot be mounted directly on the mask and, moreover, they produce an additional dead space. Moreover, they promote condensation when a humidifier is used, as a result of which their pneumatic properties may change.

SUMMARY OF THE INVENTION

The object of the present invention is to provide a breathing mask that is improved compared to the state of the art and has increased wearing comfort and increased acceptance by the user and his social environment.

The present invention is based at first on the fact that the breathing masks are fed via a specially designed strap, which considerably improves the wearing comfort. The straps, which are designed in conventional breathing masks only for absorbing the tensile forces necessary to press on the mask, are additionally used to guide the inspiratory breathing gases. The present invention comprises a breathing mask to be fastened on the head with a strap with breathing gas supply through the strap, in which the strap comprises areas that have a multilayer design and at least two layers of the material of the strap, which are located one on top of another, are connected with one another such that they form a channel, through which a gas can flow.

In an advantageous embodiment, the straps comprise an at least two-layer textile fabric, in which the layers are connected with one another such that they form longitudinally extending channels. These channels lead from the area of the mask body into the nape area of the patient. If the channel is used to feed the breathing gas, additional separate flexible tubes outside the strap for feeding the inspiratory breathing gas may be eliminated, which alone leads to a substantial improvement of the visual impression created by such a mask. It is advantageous that the layers of the material of the strap forming the channels are bonded with one another next to the particular channel. As an alternative or in addition, the connection may be brought about at the same point by sewing. Areas with one or more steps can thus be formed, as a result of which decorative effects can also be achieved with a strap according to the present invention.

The connection to the necessary respirator may be in the nape area of the patient, where two straps are brought together. The respirator may both be integrated directly in the nape area or connected with the breathing mask via conventional flexible tubes and a corresponding connection piece in the nape area of the patient. A connection piece, to which an external respirator can be connected, is located for this purpose in the nape area, and the connection piece is in connection with the interior of the mask body via the channels in the strap. The partial covering of the patient's face in the manner that is felt to be especially unpleasant, namely, the covering of the eyes or the insertion of the nose, is thus avoided. It is especially comfortable to provide a pad in the nape area. A respirator can be integrated in this pad in a simple manner. If the respirator is operated with batteries, the user of the breathing mask is independent from stationary supply units, because neither an external energy supply nor an external breathing air supply is needed.

The strapping of the mask, which is present on both sides of the head anyway, may be designed such that a channel for feeding breathing gas is present on each side. At any rate, it is advantageous if the strap comprises at least two channels on different sides of the head. It is especially advantageous if the cross section of the channels is variable. This can be achieved in a very simple manner by a sufficiently flexible design of the straps. Thus, provisions may be made for the channels to unfold only due to the pressure to be provided being applied, while they otherwise lie flat on the head. If a channel is compressed on one side by the head being placed on the side, the feed of the breathing gas through the other channel is not interrupted or hindered. As a result, there is increased wearing comfort, because the patient does not have to pay attention to the position in which he holds his head. The channels are designed now such that the maximum cross section of each of the channels is large enough to ensure the breathing gas supply through it alone. For example, a sufficient supply of the mask by a CPAP respirator can already be ensured through one channel.

Another advantageous embodiment of a mask according to the present invention comprises a special design of the mask body. The mask body consists here at least partially of a gas-permeable textile material. The expired volume flow can thus escape through textile areas of the mask body, preferably on the front side of the mask body. As a result, an expiration valve as a separate component is unnecessary. It is especially advantageous if the mask body comprises a moldable support frame, to which the textile material is fastened. The meshes in the fabric structure of the textile material form many discharge channels extending in parallel, whose size can be kept very small in the particular case. By using a relatively large area, the pneumatic resistance can likewise be kept very low. The gases being expired are discharged into the environment diffusely. Focusing of the gases being expired to a certain area of the face is thus prevented from occurring with certainty. The plurality of parallel discharge channels ensures that a sufficiently low velocity of discharge will prevail and thus there will be a laminar flow only. A great increase in the expiration resistance during heavier breathing is thus avoided, and noise generation remains low. Moreover, the direction of the discharge can be affected by the arrangement of the textile area. It is always set such that it takes place away from the patient's face. This can be advantageously achieved by the textile material of the mask body being arranged as a multilayer material in individual areas. Thus, individual areas with different numbers of layers can be formed, which have different pneumatic resistances, as a result of which the discharge geometry can be affected by the mask body. The flow resistance can thus be adapted to the standby pressure, which is preferably set, by varying the number of layers. It is also possible to form zones with different flow resistances by combining different fabric structures.

In an especially advantageous embodiment, a fabric structure with hydrophobic properties is used as the textile material. Condensation processes, which could change the pneumatic properties and the flow resistance, are thus avoided.

In an embodiment that is especially advantageous in terms of production technology, the fabric of the area of the mask body and of the strap, through which breathing takes place, consists of the same textile material. The material has open pores in the area through which breathing takes place, whereas the material can be sealed by lamination or another manner or by coating in the area of the strap in which the breathing gas is fed in, in order to prevent the gases to be fed from needlessly escaping. At any rate, it is advantageous if the material of the strap has a sealing coating at least in the area of the channels.

The present invention will be explained in greater detail on the basis of exemplary embodiments. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1 is a front schematic view of a breathing mask with an open fabric structure and a breathing gas feed led on both sides within the strap;

FIG. 2 is a side schematic view, partially in section, of an identical breathing mask on the user;

DESCRIPTION OF THE PREFERRED EMBODIMENTS

Figure 4:
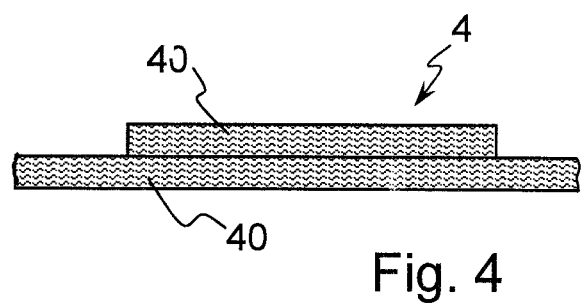
FIG. 4 is a sectional broken away view showing individual areas with different numbers of layers.

Referring to the drawings in particular, FIG. 1 shows a CPAP mask designed as a nose mask, whose mask body comprises a rigid frame 1. This frame 1 approximately defines the contact surface of the mask body on the patient's face. On the patient side, this frame 1 carries a flexible, very soft seal 2, which is supported by the internal pressure, which is provided by the CPAP respirator. On the exterior or room side, i.e., on the side finding away from the patient, the frame 1 is provided with a moldable support frame 3 in the form of a grid-like skeleton, which approximately predetermines the shape of the mask body. A nylon textile fabric 4 is mounted on the skeleton. A continuous volume flow 7, which is distributed over a very large area, which may comprise the entire surface of the mask body, is passed through the nylon fabric 4. The pneumatic resistance can be set for different conditions of use by using different mesh sizes, fabric thicknesses and a variable number of fabric layers 40 (see FIG. 4). The air being expired preferably escapes in this example through five fields of the moldable support frame 3, which is indicated by the arrows 7. The breathing gases fed in pass through a channel 5 integrated in the strap in FIG. 1 and enter the interior of the mask body from there. The breathing gases fed in may also pass through a channel 6 which is likewise integrated within the strap. FIG. 1 illustrates the two pathways with channel 6 shown in the non-unfolded (not expanded) state, which may be due, for example, to the head lying on a bed.

FIG. 2 shows the side view of an identical breathing mask. The two channels 5 and 6 are led together in the nape area of the user and end at a pad 8. In the pad 8 a connection piece 9 is integrated that acts as a plug-type connection for connecting a CPAP respirator.

Figure 3:
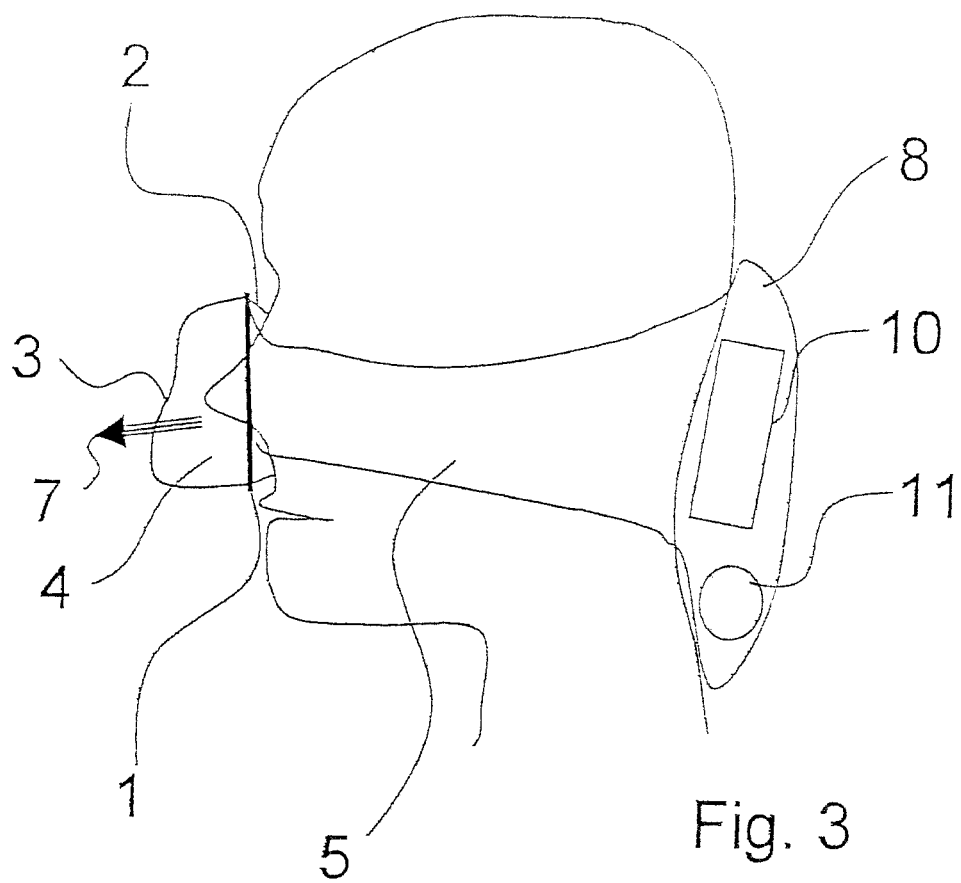
FIG. 3 is a side schematic view, partially in section , of a mask according to the present invention on the user with a respirator integrated in the nape area.

FIG. 3 additionally shows an advantageous embodiment of an otherwise identical breathing mask according to the present invention. In the embodiment of FIG. 3 a CPAP respirator 10 is integrated in the pad 8 with an energy storage means 11. The energy storage means 11 is in the form of batteries. The respirator 10 is contained in the pad 8 in the nape area instead of the connection piece provided according to the embodiment of FIG. 2.

While specific embodiments of the invention have been shown and described in detail to illustrate the application of the principles of the invention, it will be understood that the invention may be embodied otherwise without departing from such principles.

What is claimed is:

1. A breathing mask comprising:
a breathing mask body including a support frame and gas permeable material covering the support frame, said breathing mask body defining an interior space;
a strap with a first layer of material connected to a second layer of material to define a connection means for fastening the breathing mask body on the head of a user and to define a breathing gas flow channel means for delivering breathing gas from a rear region of the head of the user along a length of said breathing gas flow channel means into said interior space of said breathing mask, said strap extending along a head engaging region to a breathing mask connection location.

2. A breathing mask in accordance with claim 1, wherein said first layer of material and said second layer of material consist of a textile material.

3. A breathing mask in accordance with claim 1, wherein first layer of material and said second layer of material are bonded together.

4. A breathing mask in accordance with claim 1, wherein said first layer of material and said second layer of material are sewn together.

5. A breathing mask in accordance with claim 1, wherein said breathing gas flow channel means comprises at least two channels, with one channel on one side of the head and another channel on another side of the head.

6. A breathing mask in accordance with claim 5, wherein the maximum cross section of each of the channels is large enough to enable the breathing gas supply to take place through one of said channels alone.

7. A breathing mask in accordance with claim 1, wherein said first layer of material and said second layer of material are flexible whereby the cross section of the breathing gas flow channel means is variable.

8. A breathing mask in accordance with claim 1, further comprising a connection piece, to which an external respirator can be connected, said connection piece being located in a nape area of the strap, the connection piece being in connection with the interior space of the mask body via the channels in the strap.

9. A breathing mask in accordance with claim 8, wherein said material of said strap has a sealing coating at least in the area of the channel means whereby gas is prevented from permeating through said channel means to an exterior of said channel means.

10. A breathing mask in accordance with claim 1, further comprising a pad located in a nape area of the strap, said pad being connected to said strap, said pad having a contact surface for engaging a nape area of the user.

11. A breathing mask in accordance with claim 10, further comprising a respirator integrated in the pad in the nape area.

12. A breathing mask in accordance with claim 1, wherein said gas permeable material of the strap is comprised of a textile material joined to textile material comprising the mask body.

13. A breathing mask comprising:
a strap to fasten the breathing mask on the head of a user, the strap comprising areas having at least two textile fabric material portions disposed with facing sides and connected with one another to form a channel defined by said facing sides, said channel facing sides defining interior surfaces of said channel through which channel a gas can flow to provide a breathing gas supply through the strap; and
a mask body comprising a frame defining an interior space and a textile material covering said frame, said mask body being connected to said strap with said channel in flow connection with said interior space.

14. A breathing mask in accordance with claim 13, wherein said frame comprises a moldable support frame, to which said textile material covering said frame is fastened.

15. A breathing mask in accordance with claim 13, wherein the textile material of the mask body possesses hydrophobic properties.

16. A breathing mask in accordance with claim 13, wherein the textile material of the mask body is arranged as a multilayer material at least in some areas.

17. A breathing mask in accordance with claim 16, wherein the textile material of the mask body is arranged in different numbers of layers in individual areas.

18. A breathing mask in accordance with claim 13, wherein the textile material of the mask body is the same textile material of which the channels in the strap are formed.

19. A breathing mask comprising:
a mask body comprising a frame and a gas permeable material covering said frame and cooperating with said frame to define a mask interior;
a strap fastened to said breathing mask body, said strap and said mask body forming an annular structure to be placed around a head of a user, said strap comprising a textile material with portions of the textile material bonded together to define a support means for supporting said mask body on the head of the user and to define a breathing gas flow channel means for delivering breathing gas from a rear region of the head of the user along a length of said channel means into said mask interior.

20. A breathing mask comprising:
a mask body defining a mask body interior; and
a strap comprising a fabric material band connected to the mask body, said mask body and said strap material band together forming an annular structure to be placed around a head of a user with the strap supporting the mask body relative to the head of the user and with an exterior surface defining a user head engaging portion extending from a rear region of the head of the user toward a connection with said mask body, said material band defining a tubular channel on each side of said connection with said mask body with an interior surface defining said channel, through which a gas can flow to define a breathing gas supply through said material band of said strap to said mask body interior for delivering breathing gas through said tubular channel to said mask body interior.

21. A breathing mask in accordance with claim 20, wherein the strap fabric material is textile material comprising layers of the material of the strap bonded together forming two channels, with one channel on one side of the head and another channel on another side of the head.

22. A breathing mask in accordance with claim 21, wherein the mask body comprises a moldable support frame and textile material fastened to said support frame.

23. A breathing mask comprising:
a mask body comprising a moldable support frame and textile material fastened to said support frame, said mask body textile material being gas permeable whereby gas can flow in and out of an interior of said mask body; and
a strap extending to said mask body and connected thereto, said mask body and said strap cooperating to form an annular structure to be placed around a head of a user to support the mask body relative to the head of the user, wherein the strap comprises a textile material with portions of the strap textile material bonded together to form a tubular head first side channel and a tubular head second side channel in fluid connection with said interior of said mask body.

24. A breathing mask in accordance with claim 23, wherein the textile material fastened to said support frame is the same textile material as the strap textile material.

25. A breathing mask in accordance with claim 23, wherein the textile material fastened to said support frame is connected with the strap textile material.

* * * * *